United States Patent [19]
Deckers et al.

[11] Patent Number: 5,631,346
[45] Date of Patent: May 20, 1997

[54] THERMOMECHANICAL DEGRADATION OF POLYOLEFINS

[75] Inventors: Andreas Deckers, Flomborn; Albin Berger, Bobenheim; Jürgen Hofmann, Ludwigshafen; Roger Klimesch, Alsbach-Hähnlein; Karl-Peter Farwerck, Worms; Hilmar Ohlig, Kaiserslautern, all of Germany

[73] Assignee: BASF Aktiengesellschaft, Ludwigshafen, Germany

[21] Appl. No.: 545,115

[22] Filed: Oct. 19, 1995

[30] Foreign Application Priority Data

Oct. 21, 1994 [DE] Germany ............... 44 37 754.1

[51] Int. Cl.$^6$ ........................ C08F 6/04
[52] U.S. Cl. ............ 528/481; 528/502 C; 528/502 F
[58] Field of Search ................ 528/481, 502 C, 528/502 F

[56] References Cited

U.S. PATENT DOCUMENTS

| 3,898,209 | 8/1975 | Watson et al. | 528/502 C |
| 5,292,862 | 3/1994 | Miura et al. | 528/481 |

FOREIGN PATENT DOCUMENTS

| 1940686 | 2/1971 | Germany. |
| 1310260 | 3/1973 | United Kingdom. |

*Primary Examiner*—Thomas R. Weber
*Attorney, Agent, or Firm*—Keil & Weinkauf

[57] ABSTRACT

Polyolefins are thermomechanically degraded in a twin-screw extruder without a downstream degradation apparatus, at from 300° to 550° C. and from 1 to 100 bar and in average residence times of the reaction mixture of from 0.5 to 10 minutes, by a process in which the pressure in the twin-screw extruder is changed periodically or aperiodically with a fluctuation of from 0.5 to 30 bar. The novel process is particularly suitable for the degradation of polypropylene.

10 Claims, No Drawings

THERMOMECHANICAL DEGRADATION OF POLYOLEFINS

BACKGROUND OF THE INVENTION

1. Field of the Invention

The present invention relates to a process for the thermomechanical degradation of polyolefins in a twin-screw extruder without a downstream degradation apparatus, at from 300° to 550° C. and from 1 to 100 bar and in average residence times of the reaction mixture of from 0.5 to 10 minutes.

The present invention also relates to low molecular weight polyolefin waxes obtainable by the novel process and to their use as materials in cosmetics, in the surface coatings sector, in the printing sector and for toners.

2. Description of the Related Art

The preparation of polyolefin waxes, in particular polypropylene waxes, in a broad molecular weight range in combination with a narrow molecular weight distribution by controlled polymerization by an economical method has not been possible to date. Such waxes are therefore predominantly obtained by thermal degradation of high molecular weight polyolefins ((U.S. Pat. No. 3,087,922, FR-A 1 289 767, FR-A 1 252 635, FR-A 1 425 695, U.S. Pat. No. 3,519,609, U.S. Pat. No. 3,562,788, CA-A 797 293, DD-A 50 113).

DE-C 3 003 768 discloses a process for the preparation of polyolefin wax, in which a mixture of polyethylene and polypropylene is thermally degraded inside a heated reactor, in particular a heated metal tube. The heated metal tube is divided into two different zones which differ in that the reaction media are present in them in one case in a homogeneous state and in the other case in a heterogeneous state. In this process, the heat energy required for the thermal degradation is applied to the reaction medium by heating the two zones to different extents.

Furthermore, DE-B 1 940 686 describes a process for the continuous preparation of waxy, low molecular weight polyethylene from solid high molecular weight polyethylene, the high molecular weight polyethylene melted in an extruder being transferred to a heated tube where it undergoes thermal degradation. In this patent, it is stated, inter alia, that an additional pressure can be established at the end of the heated tube by means of a valve or a nozzle, against which pressure the polyethylene is extruded.

EP-A 0 474 889 likewise discloses a process for the thermal decomposition of polymers, in particular polyolefins, in which the polymer is first melted in an extruder and the molten polymer thus obtainable is then subjected to thermal decomposition in a tube reactor. The tube reactor used may also be provided with a static mixer in order thus to achieve more effective decomposition of the polymer.

The literature furthermore describes a process for the thermomechanical degradation of polyisobutylene/polystyrene blends [F. P. La Mantia, M. A. Nocilla in Polymer Degradation and Stability 17 (1987), 279–286]. This publication reveals in particular that the degradation of plastics blends can be influenced both by the supply of heat energy and by the supply of mechanical energy.

However, the waxes obtained in this process frequently have a number of disadvantages, for example the yellow coloration of the end product or high contents of byproducts, for example soot particles. In addition, the formation of wall deposits and caking are often observed in this process, particularly during continuous operation. In the preparation of very low molecular weight polyolefin waxes, very long residence times also generally have to be accepted, giving rise to high costs. Moreover, an increasing residence time, ie. an increasing degree of degradation, leads to increasing discoloration. Furthermore, the processes known to date often cannot be exactly controlled and lead to high contents of soot particles, especially in the degradation of polypropylene. The low molecular weight polypropylenes thus obtained frequently contain many, generally aperiodically distributed soot particles, which are disadvantageous with regard to subsequent use, for example in masterbatches.

SUMMARY OF THE INVENTION

It is an object of the present invention to provide a novel process which permits the degradation of polyolefins while avoiding the known disadvantages and which is distinguished by exact controllability of the degradation reaction and by a very low level of formation of byproducts, in particular of soot particles.

We have found that this object is achieved by a process for the thermomechanical degradation of polyolefins in a twin-screw extruder without a downstream degradation apparatus, at from 300° to 550° C. and from 1 to 100 bar and in average residence times of the reaction mixture of from 0.5 to 10 minutes, which comprises changing the pressure in the twin-screw extruder periodically or aperiodically with a fluctuation of from 0.5 to 30 bar.

In the novel process, the degradation of polyolefins is carried out thermomechanically, ie. the energies required for cleaving the polymer chains are supplied to the polyolefins both in the form of thermal energy and in the form of mechanical energy. The thermomechanical degradation is carried out in a twin-screw extruder without a downstream degradation apparatus, for example a heated tube. Suitable twin-screw extruders are those which are usually used in the plastics industry and are manufactured by, inter alia, Werner & Pfleiderer, Berstorff, Leistritz, JSW or Toshiba.

DESCRIPTION OF THE PREFERRED EMBODIMENTS

The thermomechanical degradation is carried out at from 300° to 550° C., in particular from 350° to 500° C., and from 1 to 100, in particular from 5 to 50, bar and in average residence times of the reaction mixture of from 0.5 to 10, in particular from 0.5 to 6, minutes. In a particularly preferred variant of the novel process, the thermomechanical degradation is carried out at from 370° to 470° C. and in average residence times of from 0.5 to 4 minutes.

In the novel process, the pressure in the twin-screw extruder is changed periodically or aperiodically with a fluctuation of from 0.5 to 50 bar. In the novel process, the pressure in the twin-screw extruder is advantageously changed periodically or aperiodically with a fluctuation of from 0.5 to 10, in particular from 1 to 5, bar.

It is advisable to carry out the novel process in such a way that the interval between two pressure surges is from 1 to 2000, in particular from 30 to 500, seconds. The individual pressure surges are triggered, inter alia, by a control apparatus or by a pressure relief valve which is provided with a timing circuit, or by slight change in the throughput. The periodically or aperiodically triggered pressure surges produce in the extruder pressure changes which in particular eliminate the formation of deposits on the extruder walls. The pressure changes are preferably effected periodically.

The novel process is carried out in particular in such a way that from 15 to 70% of the energy required for degrading the polyolefins are introduced into the twin-screw extruder in the form of mechanical energy. In the novel process, advantageously from 20 to 60%, in particular from 25 to 60%, of the energy required for degrading the polyolefins are supplied to the polyolefins in the form of mechanical energy. The supply of mechanical energy can be controlled in particular by the speeds of the extruder screws. These are usually from about 100 to 500, in particular from 200 to 350, revolutions per minute.

In the novel process, it may be advisable to divide the twin-screw extruder to be used into two different zones, a melting zone (I) and a downstream zone containing a homogeneous phase (II). The twin-screw extruder is usually divided by means of shearing elements, for example kneading blocks. An additional pressure of from 1 to 50, in particular from 1 to 30, bar is preferably applied in the second zone containing a homogeneous phase (II). This pressure is the pressure applied at the extruder discharge by means of appropriate valves or nozzles. The additional pressure is to be distinguished from the pressure which is built up in the system by the reactants and in particular by their flow resistance. Among other things, the foam formation of the volatile products formed during the degradation reaction is suppressed and the thermal conductivity of the reaction mixture is improved by application of the additional pressure. This has a positive effect on the quality of the resulting low molecular weight polyolefin waxes.

The twin-screw extruders used for degradation of the polyolefins can generally be divided into at least two zones for an optimum procedure. Different pressure and temperature conditions may be established in the individual zones. The screw combinations present in the interior of the twin-screw extruder are co-rotating or counter-rotating and intermeshing and their design is adapted to the particular working conditions in the individual sections of the extruder. The choice of the suitable screws or screw elements, the speeds and the geometry of the twin-screw extruder, ie. its length/diameter ratio, depends on, inter alia, the particular transport conditions and the particular polyolefins used and are familiar to a person skilled in the art from his technical knowledge.

In the novel process, the polyolefins to be degraded are preferably first introduced via a feed orifice into a melting zone (I) and transferred from there in the form of a melt into a zone containing a homogeneous phase (II), the degradation reaction starting in the melting zone itself. The low molecular weight polyolefins obtainable thereby are then transported via the discharge orifice out of the twin-screw extruder and worked up, ie. cooled, devolatilized and compounded, there.

The novel process can advantageously be designed in such a way that 80% of the mechanical energy introduced into the twin-screw extruder are supplied in the melting zone (I). In a particularly preferred process, as much as at least 90% of the mechanical energy introduced into the twin-screw extruder are supplied in the melting zone (I) itself. Among other things, good back-mixing of the polyolefins in the melting zone (I) and good dissipation are achieved in this way.

The zone containing homogeneous phase (II) is distinguished in particular by thorough axial mixing and a low level of back-mixing of the melt. In the zone containing a homogeneous phase (II), the final degree of degradation of the polyolefin can be exactly controlled by the temperature program and the pressure.

In the novel process, the division into a melting zone (I) and a zone containing homogeneous phase (II) can be realized both in a single twin-screw extruder and in two or more twin-screw extruders connected in series. The degradation of the polyolefins is preferably carried out in a single twin-screw extruder.

The novel process is particularly suitable for the thermomechanical degradation of polyolefins. The term polyolefins is to be understood in this context as meaning in particular homopolymers of ethylene, of propylene and of isobutylene. This term also covers copolymers of these monomers with other comonomers, for example with $C_4$–$C_8$-αα-olefins, such as but-1-ene, pent-1-ene or hex-1-ene, and with vinylaromatic comonomers, for example with styrene. The polyolefins used can of course also be copolymers of propylene with ethylene and/or further $C_4$–$C_8$-α-olefins, for example but-1-ene. These polyolefins in recycled form and mixtures thereof with other plastics can also be degraded.

Homo- and copolymers of ethylene and of propylene are known to a person skilled in the art and are described in the literature, and reference may therefore be made to the relevant publications with regard to detailed information on the preparation and on the composition. Such polymers are usually obtainable by Ziegler-Natta polymerization, by polymerization with chromium-containing Phillips catalysts, by high pressure polymerization in the presence of free radical initiators or by polymerization with metallocene-containing catalysts (EP-A 45 977, U.S. Pat. No. 4,857,613, U.S. Pat. No. 5,100,978, EP-A 323 716). The polymerization can be carried out in the gas phase, in suspension or in solution. Such polyolefins are obtainable, inter alia, under the tradenames NOVOLEN® and LUPOLEN® from BASF Aktiengesellschaft.

Such polymers generally have weight average molecular weights of from 100,000 to 1,000.000 and melt flow indices of from 0.1 to 100, preferably from 0.2 to 80, g/10 min, measured in each case according to DIN 53 735 at 230° C. and 2.16 kg. The melt flow index corresponds to the amount of polymer which is forced in the course of 10 minutes, at 230° C. and under a weight of 2.16 kg, out of the test apparatuses standardized according to DIN 53 735.

The homo- and copolymers of isobutylene are prepared in particular by continuous cationic polymerization by the belt method (Ullmans Encyklopädie der Technischen Chemie, Volume 19, page 220, 4th Edition, Verlag Chemie GmbH, Weinheim [1980]). The isobutylene in pure dried, liquid ethylene is subjected to cationic polymerization on a slightly inclined, continuous steel belt. The polyisobutylenes obtainable in this manner have viscosity-average molecular weights ($\overline{M}_v$) of from $0.1 \cdot 10^6$ to $10 \cdot 10^6$. They are obtainable under the tradename OPPANOL® from BASF Aktiengesellschaft.

The novel process gives low molecular weight polyolefin waxes having weight average molecular weights $\overline{M}_w$ of from 1,500 to 60,000, in particular from 3,000 to 40,000, which are also referred to as waxes. The novel process is particularly suitable for the preparation of low molecular weight propylene homopolymers and low molecular weight propylene copolymers, which are distinguished from the prior art low molecular weight polyolefins by, inter alia, substantially less yellowing and greatly reduced contents of byproducts, in particular of soots. Low molecular weight propylene homopolymers are to be understood as meaning both isotactic and syndiotactic and atactic propylene homopolymers. Suitable low molecular weight propylene copolymers are in particular random propylene copolymers with minor amounts of other α-olefins, for example of ethylene and/or but-1-ene.

The novel process is in particular readily controllable. Compared with the degradation processes known to date, it is less complicated in terms of process engineering since downstream degradation apparatuses and dwell units need not be used. Moreover, the thorough mixing in the twin-screw extruder and the pressure changes result in greater self-purging, which suppresses the formation of deposits on the reactor wall. As a result of these measures, inter alia, the polyolefin chains are preferentially cleaved in the middle of the chain, whereas in a purely thermal cleavage the cleavage points are randomly distributed.

In the novel process, it is particularly surprising that a reduction in the discoloration is achieved when the degree of degradation is increased by generating an additional pressure. These measures result in low molecular weight polyolefins which are distinguished in particular by a reduced content of byproducts. They are used, inter alia, as waxes in cosmetics, in the surface coatings sector, in the printing sector and as toners.

EXAMPLES

Examples 1 and 2 as well as the comparative example were carried out in a ZSK 53 twin-screw extruder from Werner & Pfleiderer. The twin-screw extruder was divided into a melting zone (I) and a zone containing a homogeneous phase (II). The twin-screw extruder used had a length/diameter ratio of 36.

Example 1

In the abovementioned twin-screw extruder, 50 kg/h of an isotactic propylene homopolymer having a melt flow index of 11 g/10 min at 230° C. and 2.16 kg according to DIN 53 735 (NOVOLEN® 1100 N from BASF Aktiengesellschaft) were extruded at 420° C. and 250 revolutions per minute. The average residence time was 2 minutes. In the zone containing a homogeneous phase (II), an average pressure of 22 bar was applied. 6.5 kW (37.1% of the total energy) were introduced into the twin-screw extruder in the form of mechanical energy, and 11 kW in the form of thermal energy by heating. The pressure was changed periodically every 5 minutes by 2 bar by means of a control apparatus.

After leaving the extruder, the resulting degradation product was cooled to 250° C., devolatilized and compounded by tableting.

The polypropylene wax obtained in this manner had a molecular weight $\overline{M}_w$ of 14,000, a molecular weight distribution Q of 2.2 and a melt viscosity of 104 cst. (determined according to DIN 51 562). The Yellowness Index acccording to ASTM D 1925 was 2.9, measured with tablets.

Example 2

Example 1 was repeated under identical conditions, the temperature now being 400° C. The total pressure in zone (II) was brought to 19 bar and the periodic pressure change was 0.5 bar.

The polypropylene wax obtained in this manner had a molecular weight $\overline{M}_w$ of 21,000, a molecular weight distribution Q of 2.3 and a melt viscosity of 996 cst. (determined according to DIN 51 562). The Yellowness Index according to ASTM D 1925 was 2.1, determined with tablets.

COMPARATIVE EXAMPLE

Example 2 according to the invention was repeated under otherwise identical conditions, but no pressure change was carried out in zone (II), so that the pressure there was constant at 19 bar.

The polypropylene wax obtained in this manner had a molecular weight $\overline{M}_w$ of 21,500, a molecular weight distribution Q of 2.3 and a melt viscosity of 1004 cst (determined according to DIN 51 562). The Yellowness Index according to ASTM D 1925 was 2.9.

Furthermore, the product quality of the polypropylene waxes obtained in Examples 1 and 2 according to the invention and in the comparative example was visually assessed with cast panels measuring 5 cm×5 cm×0.3 cm, with regard to the black colorations due to soot particles. The assessment was carried out on the basis of a decreasing rating system in which 1 means particularly pure polypropylene waxes and 6 means polypropylene waxes particularly contaminated with soot particles. Samples were determined after an extruder run-time of 1 hour and 5, 12, 24 and 48 hours. The results in each case are shown in the table below.

TABLE

| Example 1 | | | | | |
|---|---|---|---|---|---|
| Reactor run-time [hours] | 1 | 5 | 12 | 24 | 48 |
| Number of soot particles [rating] | 2 | 2 | 2 | 2 | 2 |
| Example 2 | | | | | |
| Reactor run-time [hours] | 1 | 5 | 12 | 24 | 48 |
| Number of soot particles [rating] | 1–2 | 2 | 2 | 2 | 2 |
| Comparative Example | | | | | |
| Reactor run-time [hours] | 1 | 5 | 12 | 24 | 48 |
| Number of soot particles [rating] | 2 | 2 | 2–3 | 3 | 4 |

The table shows that, particularly in the case of relatively long extruder run-times, the novel process leads to polypropylene waxes having a substantially lower content of soot particles, which is manifested in terms of an improved visual impression (better ratings).

We claim:

1. A process for the thermomechanical degradation of polyolefins consists essentially of a twin-screw extruder without a downstream degradation apparatus, at from 300° to 550° C. and from 1 to 100 bar and in average residence times of the reaction mixture of from 0.5 to 10 minutes, wherein the pressure in the twin-screw extruder is changed periodically with a fluctuation of from 0.5 to 30 bar.

2. A process as claimed in claim 1, wherein the pressure in the twin-screw extruder is changed periodically with a fluctuation of from 0.5 to 10 bar.

3. A process as claimed in claim 1, wherein the interval between two pressure changes is from 1 to 2000 seconds.

4. A process as claimed in claim 1, wherein the thermomechanical degradation is carried out at from 350° to 500° C.

5. A process as claimed in claim 1, wherein the thermomechanical degradation is carried out in average residence times of the reaction mixture of from 0.5 to 6 minutes.

6. A process as claimed in claim 1, wherein the twin-screw extruder is divided into at least two zones, a melting zone (I) and a zone containing a homogeneous phase (II), an additional range of fluctuation of from 1 to 50 bar furthermore being generated in the second zone (II).

7. A process as claimed in claim 1, wherein from 15 to 70% of the energy required for the degradation of the polyolefins is imparted by the twin-screw extruder in the form of mechanical energy to the reaction mass.

8. A process as claimed in claim 1, which is used for the degradation of propylene homopolymers and of propylene copolymers.

9. A low molecular weight polyolefin wax, obtained by a process as claimed in claim 1.

10. Process for the production of materials in cosmetics, in the surface coatings sector, in the printing sector or for toners, wherein a low molecular weight polyolefin wax as claimed in claim 9 is used.

* * * * *